United States Patent
Al-Harbi (10) Patent No.: US 10,522,052 B2
(45) Date of Patent: Dec. 31, 2019

(54) METHOD, SYSTEM AND DEVICE FOR INDICATING THE PRESSURE PATTERN BY THE TONGUE FOR CORRECT PRONUNCIATION

(71) Applicant: Alaa S. G. H. S. S. Al-Harbi, Sabah Al-Salem (KW)

(72) Inventor: Alaa S. G. H. S. S. Al-Harbi, Sabah Al-Salem (KW)

( * ) Notice: Subject to any disclaimer, the term of this patent is extended or adjusted under 35 U.S.C. 154(b) by 297 days.

(21) Appl. No.: 14/337,471

(22) Filed: Jul. 22, 2014

(65) Prior Publication Data

US 2016/0027332 A1 Jan. 28, 2016

(51) Int. Cl.
*G09B 19/04* (2006.01)
*A61B 5/00* (2006.01)

(52) U.S. Cl.
CPC ............ *G09B 19/04* (2013.01); *A61B 5/4803* (2013.01); *A61B 5/682* (2013.01)

(58) Field of Classification Search
CPC .................................................... G09B 19/04
USPC ........................................................ 434/185
See application file for complete search history.

(56) References Cited

U.S. PATENT DOCUMENTS

| | | | |
|---|---|---|---|
| 4,112,596 A * | 9/1978 | Fletcher et al. | 600/590 |
| 4,175,338 A | 11/1979 | Takinishi et al. | |
| 4,287,895 A | 9/1981 | Hori | |
| 6,511,441 B1 | 1/2003 | Wakumoto et al. | |
| 6,945,778 B2 * | 9/2005 | Jacobs et al. | 433/37 |
| 6,971,993 B2 * | 12/2005 | Fletcher | 600/587 |
| 2009/0186324 A1 * | 7/2009 | Penake et al. | 434/185 |
| 2009/0239201 A1 | 9/2009 | Moe | |

OTHER PUBLICATIONS

"Palatal Tongue Controller," Clayton et al., Journal of Microcomputer Applications (1992), pp. 9-12.*

* cited by examiner

*Primary Examiner* — Sean K. Hunter
*Assistant Examiner* — Jennifer L Korb
(74) *Attorney, Agent, or Firm* — Hauptman Ham, LLP (57) ABSTRACT

A tongue pressure indicating device for the correct pronunciation of a selected letter in a preselected language includes a thin palate plate in the general shape of an individual's palate and sized to fit immediately under the individual's palate and in conformity therewith, a metal wire supports the palate plate positioned under the individual's palate. The palate plate includes a plurality of downwardly projecting stubs for indicating the position where the individual's tongue touches the individual's palate for the correct pronunciation of a specific letter in a preselected language. A method for teaching the correct pronunciation is also disclosed.

20 Claims, 8 Drawing Sheets

FIG. 4 shows the sound for letter (Zai)

FIG. 5 shows the sound for letter (Sa)

FIG. 6 shows the sound for letter (Sad)

FIG. 7 shows the sound for letter (Tha)

FIG. 8 shows the sound for letter (Thah)

FIG. 9 shows the sound for letter (Tah)

FIG. 10 shows the sound for letter (Thah)

FIG. 11 shows the sound for letter (Dah)

FIG. 12 shows the sound for letter (Tah)

FIG. 13 shows the sound for letter (La)

FIG. 14 shows the sound for letter (Na)

FIG. 15 shows the sound for letter (Rah)

FIG. 16 shows the sound for letter (Ga)

FIG. 17 shows the sound for letter (Sha)

FIG. 18 shows the sound for letter (Ya)

FIG. 19
shows the sound for letter (Dad)

FIG. 20
shows the sound for letter (Kah)

METHOD, SYSTEM AND DEVICE FOR INDICATING THE PRESSURE PATTERN BY THE TONGUE FOR CORRECT PRONUNCIATION

FIELD OF THE INVENTION

This invention relates to a method, system and device for indicating the pressure pattern by the tongue against an individual's palate for the correct pronunciation of a specific letter in a preselected language and more particularly to one of 17 letters in the Arabic alphabet. The invention also relates to a method and system for training an individual to speak a preselected language with the correct pronunciation.

BACKGROUND FOR THE INVENTION

It is well known that contact of an individual's palate is an important factor for correctly pronouncing a consonant in the English language. It is also well known that the correct pressure pattern of an individual's tongue against the individual's palate or generally roof of the mouth contributes to the correct or proper pronunciation of selected letters in preselected languages.

For example, a U.S. Patent of Wakumoto et al. U.S. Pat. No. 6,511,441 discloses a System for Measuring Tongue Pressure. As disclosed, a system for measuring tongue pressure includes a thin palate floor plate, thin pressure sensor sheets, an attaching member and a cable. The shape of the thin palate floor plate matches with that of a palate. The thin pressure sensor sheets have a plurality of pressure sensing cells secured to the lower surface of the palate floor plate. The attaching member attaches the palate floor plate to a proper position on the palate.

The cable transmits information from the pressure sensing cells of the pressure sensor sheets to an apparatus outside the palate, and is let out of the oral cavity extending around the back of the final gum tooth and passing along the vestibule of the oral cavity when the palate floor plate is attached on the palate. Each of the pressure sensor sheets has two resin backings structured in one body, each of which has a plurality of electrodes covered with a pressure-sensitive ink layer on one side. Between the backings, air is contained gastightly. The electrodes are opposed to each other via the pressure-sensitive ink. The portions corresponding to the opposing electrodes and the pressure-sensitive ink layer functions as the pressure sensing cells.

A slightly more recent U.S. Patent of Fletcher U.S. Pat. No. 6,971,993 discloses a Method for Utilizing Oral Movement and Related Events. As disclosed, a method for utilizing oral movements is used in speech assessment, speech therapy, language development, and controlling external devices. A device is used which includes a sensor plate having sensors to detect contact of the tongue with the sensor plate. One aspect of the invention allows viewing representations of contact of the tongue and palate during speech and comparing the representations with model representations displayed in a split screen fashion. The model representations may be generated by another speaker utilizing a sensor plate or by computer generated representations which have been electronically stored. The representations may be analyzed to assess speech proficiency and the model may be mimicked for speech enhancement.

Finally, a U.S. Patent Publication of Moe No. 2009/0239201 discloses a Phonetic Pronunciation Training Device, Phonetic Pronunciation Training Method and Phonetic Pronunciation Training Program. As disclosed therein, a phonetic pronunciation training device, phonetic pronunciation training method, and phonetic pronunciation training program are provided wherein pronunciation and sounds in language acquisition can be self-learned and listening skills, spelling skills and vocabulary can be enhanced. The present invention comprises at least a data base for storing phonetic pronunciation data associated with phonetic data and phonetic symbol data indicating this phonetic data, a selection function block for receiving instruction signals from an input means and randomly selecting phonetic pronunciation data, a phonetic pronunciation data reproducing function for reproducing selected phonetic pronunciation data, and a phonetic symbol data correct/error determination function block for comparing phonetic symbol data input by the input means and phonetic symbol data corresponding to the selected phonetic pronunciation data and recording the correct/error result to a memory means.

Notwithstanding the above, it is presently believed that there is a need and a potential commercial market for an improved method, system and device for indicating the proper pressure pattern by the tongue against an individual's palate or palate plate for pronouncing a specific letter in a preselected language. There should be a commercial market because the device allows an individual to feel the proper tongue position against the individual's palate for correctly pronouncing a letter in a preselected language, as for example one of 17 letters in the Arabic language. The method, system and device in accordance with the present invention are relatively simple in design and manufacture and can be readily reproduced for use by adults and children with different sized mouths.

SUMMARY OF THE INVENTION

In essence, a tongue pressure indicating device for the correct pronunciation of a letter in a preselected language comprises or consists of:

a relatively thin palate plate in the general shape of an individual's palate and sized to fit in the individual's mouth immediately below the individual's palate and in conformity therewith. Means such as a metal wire like form fix the palate plate positioned in the individual's mouth.

The palate plate includes a plurality of pressure indicating points such as a plurality of downwardly projecting rod like stubs in a pattern of where the tongue should contact the palate plate for the correct pronunciation of a selected letter in a preselected language.

In a preferred embodiment of the invention a tongue pressure indicating method for teaching an individual to correctly pronounce a specific letter in a preselected language comprises or consists of:

providing a relatively thin rigid or semi rigid palate plate sized to fit behind an individual's front teeth immediately under an individual's palate and sized and dimensioned to generally conform to the individual's palate;

placing, positioning said palate plate in the mouth of the individual under the plate of the individual;

wherein the palate plate includes a grid of at least 6 to 8×8 pressure indicating points indicating a pattern of tongue contacting palate indicators for pronouncing a selected letter in a preselected language; and instructing the individual to repeat sound of the selected letter with their tongue in contact with the palate plate as indicated by the palate plate.

The invention will now be described in connection with the accompanying figures wherein like reference numerals have been used to identify like parts.

DESCRIPTION OF THE PREFERRED EMBODIMENTS OF THE INVENTION

Figure 1:
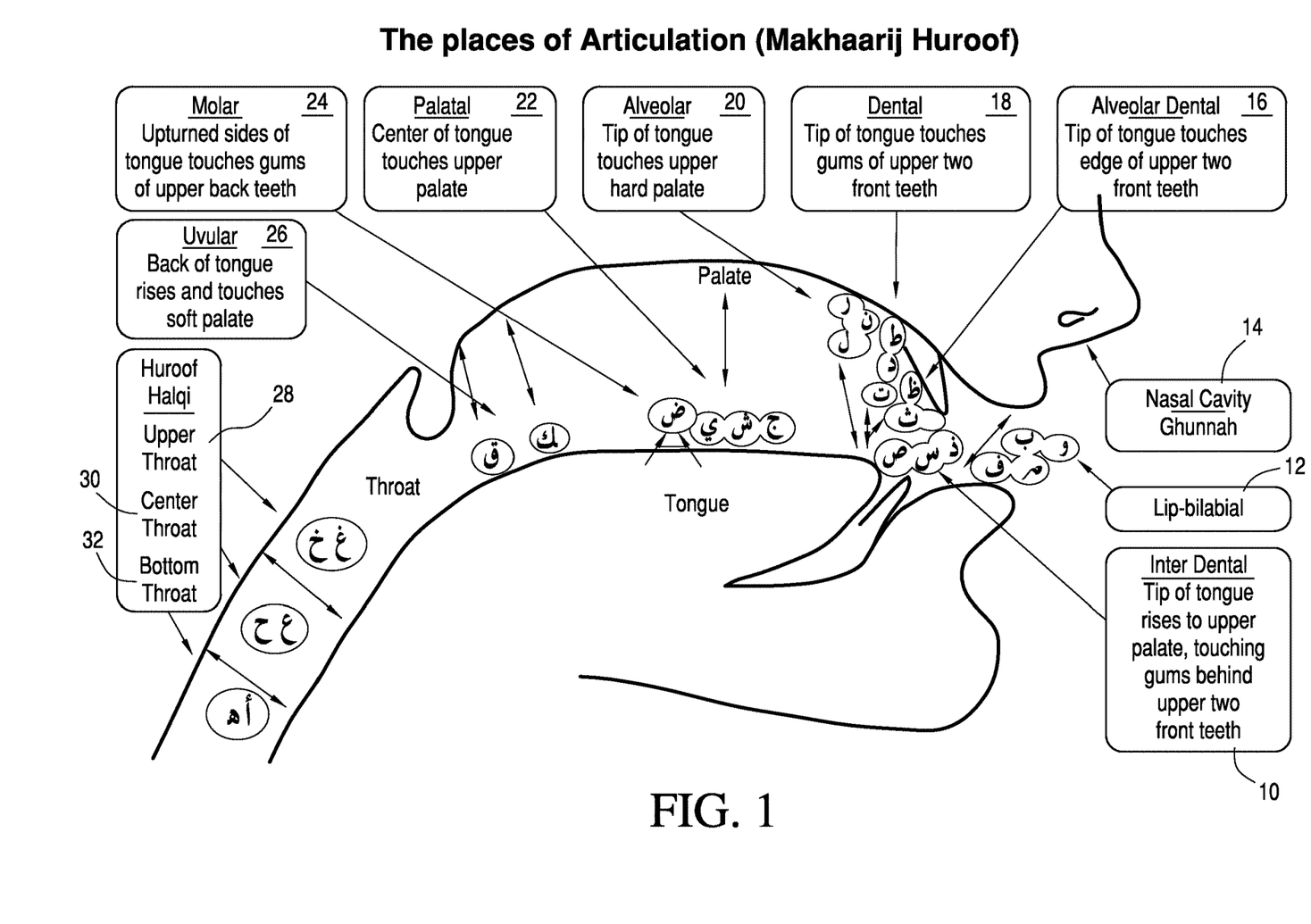
FIG. 1 is a schematic illustration of a lower portion of an individual's face and chin including a cross section of the individual's mouth, palate and throat.

Referring now to FIG. 1, the places of articulation (Makhaarij Huroof) are indicated. To be more specific, the places where an individual's tongue contacts or presses against the roof of the mouth for the proper pronunciation of one of 17 letters in the Arabic alphabet. The 17 letters in the Arabic alphabet have been used as an example since the original work by the Applicant was done on the proper pronunciation of the Arabic letters. However, it should be recognized that the principles of the present invention apply to specific letters in many other languages.

The specific areas of an individual's mouth have been identified as uvular, palatal, molar, alveolar, dental, alveolar dental, inter dental, and bilabial. As shown in FIG. 1, an individual's mouth, lips, front teeth, palate and throat are indicated.

An inter dental area 10 is with the tip of the individual's tongue rising to the upper palate touching the gums behind the two upper front teeth. Also shown is the lip-bilabial area 12 and nasal cavity 14. The alveolar dental area 16 is with the tip of the tongue touching the edge of the upper two front teeth. In addition, the dental area 18 is with the tip of an individual's tongue touching the gum of the two upper front teeth.

Moving rearward in an individual's mouth, the alveolar area 20 is with the tip of the tongue touching the hard palate. The alveolar area 20 is followed by the palatal area 22 wherein the center of the tongue touches the upper palate. The palatal area 22 is followed by the molar area 24 wherein the upturn sides of the tongue touch the gums of the upper back teeth. Further back, the uvular area 26 is where the back of the tongue rises and touches the soft palate. Subsequently, the uvular area 26 is followed by the upper throat 28, center 30 and bottom throat 32.

Figure 2:
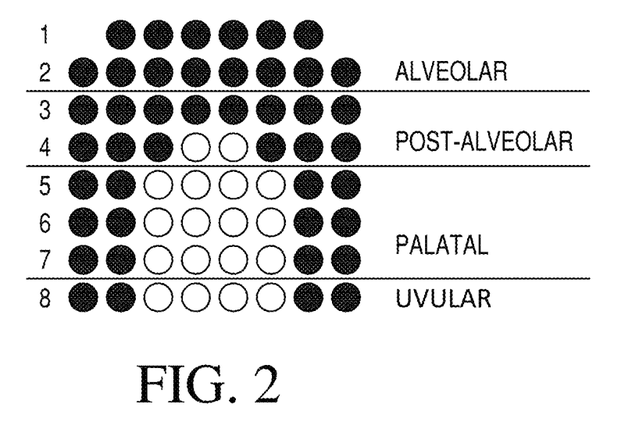
FIG. 2 is a schematic illustration of a series of pressure points and their positions for a tongue pressure indicating device.

FIG. 2 illustrates a plurality of rows and columns of downward projections on a palate plate of the type used to indicate tongue placement for the proper pronunciation of a letter in a preselected language. The palate plate includes a plurality of non-electrical pressure indicating points for indicating the proper position of the individual's tongue against the palate plate for the correct pronunciation of a specific letter in a specific language. As shown, the solid color downward projections are about ⅛ inch length while the partially shaded circles (not shown in FIG. 1, 2, 3, 13 or 20) of relatively short stubs have a length of 1/16 inch or less and are partially obscured and appear to be gray. By contrast, the uncolored ovals have no downward projections or the projections have been removed. As indicated, the downward projections are placed in the various areas of an individual's mouth as for example alveolar, post alveolar, palatal and uvular areas. As shown, there are three or more rows of downward projections having a length of ⅛ of an inch or short stubs having a length of 1/16 inch and six to eight symmetrical columns.

While shown as an 8×8 pattern it should be recognized that in one embodiment of the invention may have oval shaped projections with a width of about 1/16 inch and height of about ⅛ inch and cover an area of up to about 3 inches by 1.5 inches or smaller if used for a youthful student.

Figure 3:
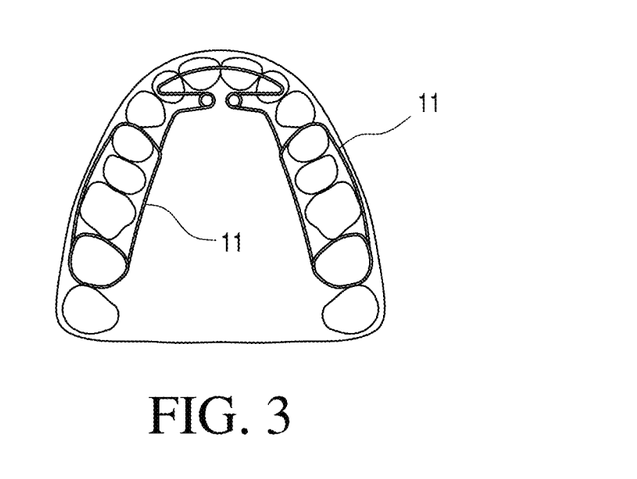
FIG. 3 is a bottom view looking upward at a support for a palate plate as positioned in an individual's mouth.
Figure 4:
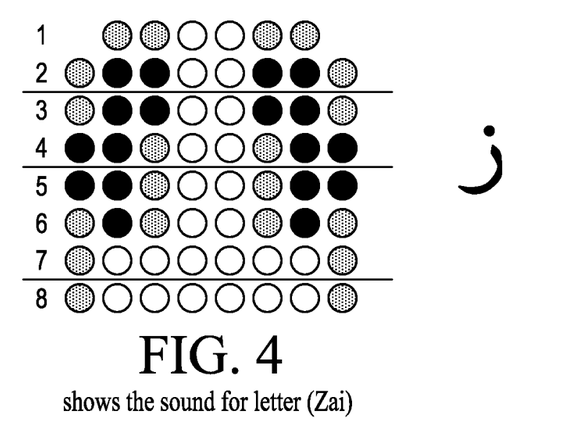
FIG. 4 is a bottom view looking upward at a plurality of pressure points on a palate plate for a first Arabic letter (Zai)
Figure 5:
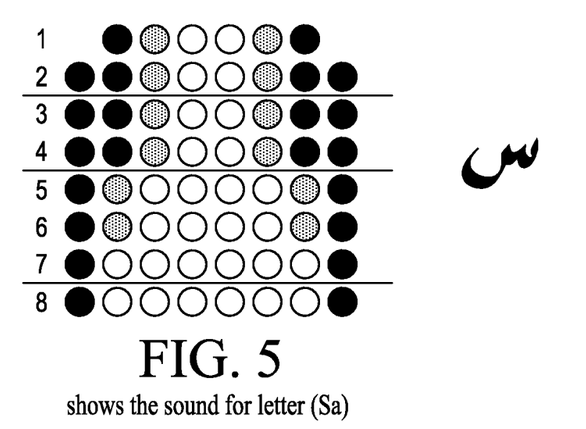
FIG. 5 is a bottom view looking upward at a plurality of pressure points on a palate plate for a second Arabic letter (Sa)
Figure 6:
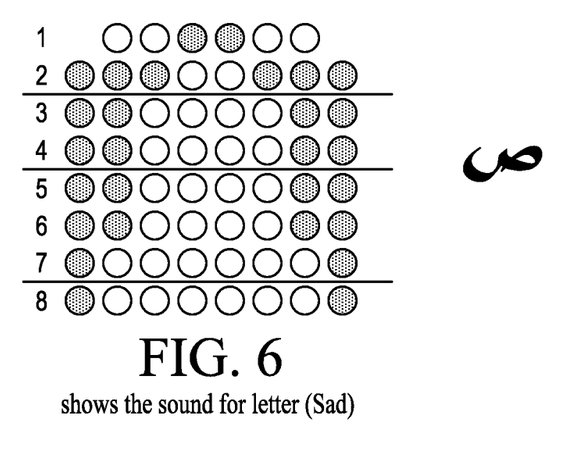
FIG. 6 is a bottom view looking upward at a plurality of pressure points on a palate plate for a third Arabic letter (Sad)
Figure 7:
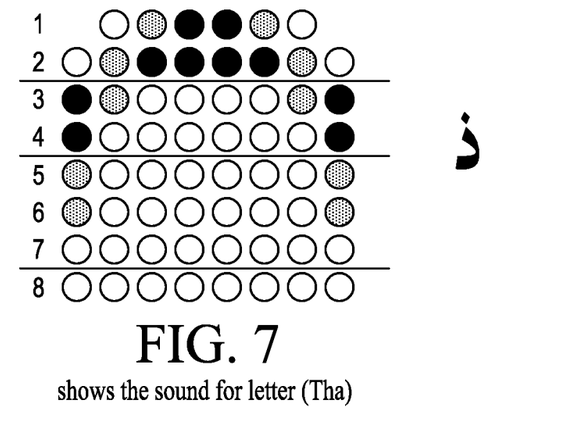
FIG. 7 is a bottom view looking upward at a plurality of pressure points on a palate plate for a fourth Arabic letter (Tha)
Figure 8:
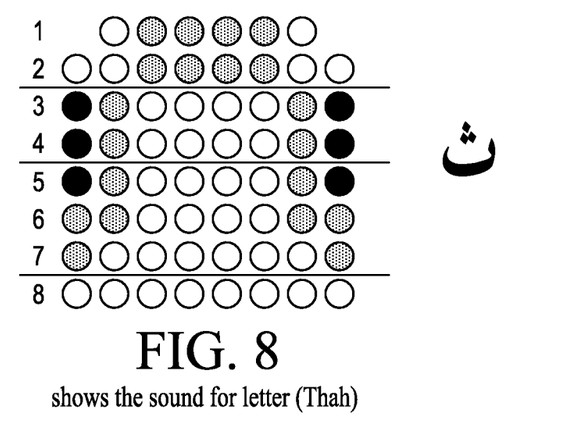
FIG. 8 is a bottom view looking upward at a plurality of pressure points on a palate plate for a fifth Arabic letter (Thah)
Figure 9:
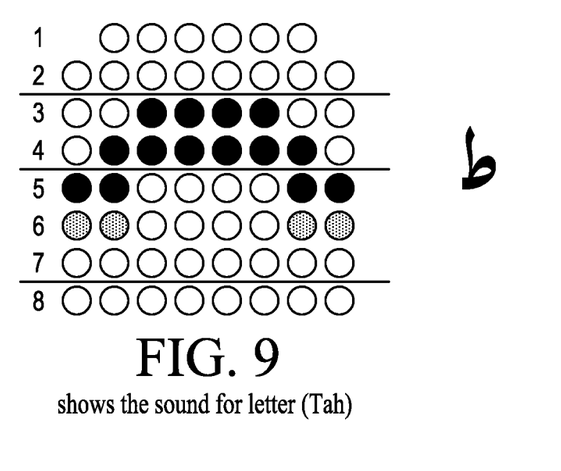
FIG. 9 is a bottom view looking upward at a plurality of pressure points on a palate plate for a sixth Arabic letter (Tah)
Figure 10:
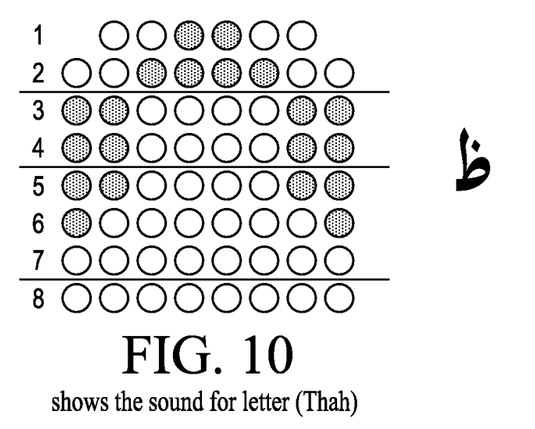
FIG. 10 is a bottom view looking upward at a plurality of pressure points on a palate plate for a seventh Arabic letter (Thah)
Figure 11:
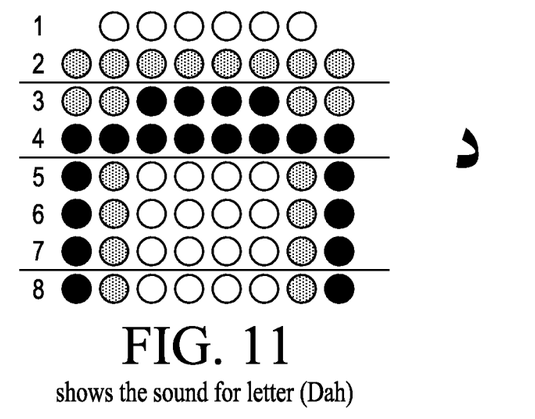
FIG. 11 is a bottom view looking upward at a plurality of pressure points on a palate plate for an eighth Arabic letter (Dah)
Figure 12:
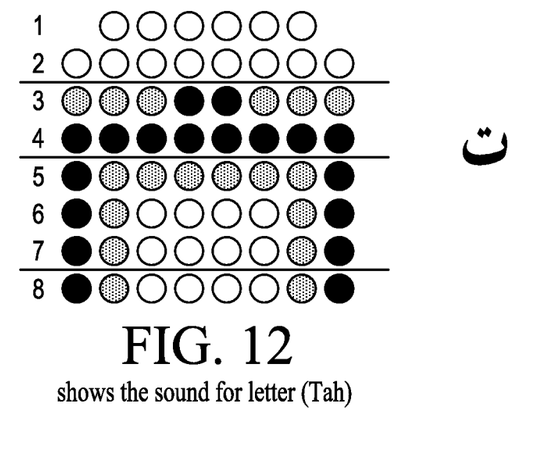
FIG. 12 is a bottom view looking upward at a plurality of pressure points on a palate plate for a ninth Arabic letter (Tah)
Figure 13:
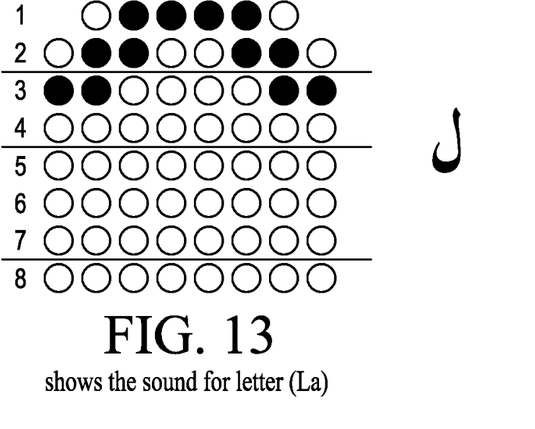
FIG. 13 is a bottom view looking upward at a plurality of pressure points on a palate plate for a tenth Arabic letter (La)
Figure 14:
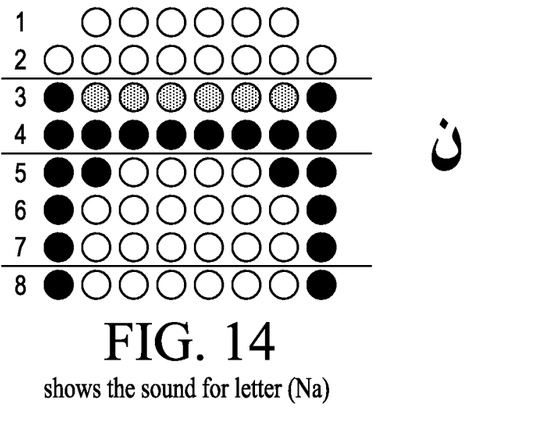
FIG. 14 is a bottom view looking upward at a plurality of pressure points on a palate plate for a eleventh Arabic letter (Na)
Figure 15:
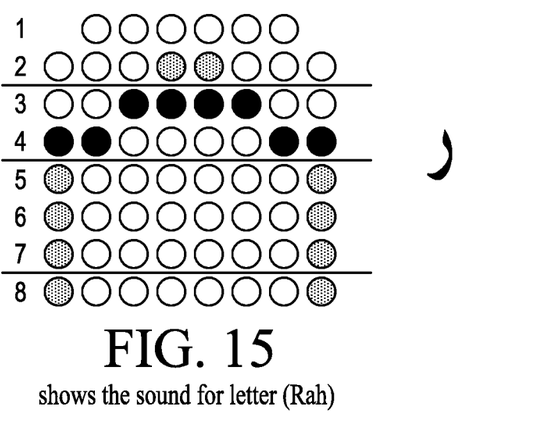
FIG. 15 is a bottom view looking upward at a plurality of pressure points on a palate plate for a twelfth Arabic letter (Rah)
Figure 16:
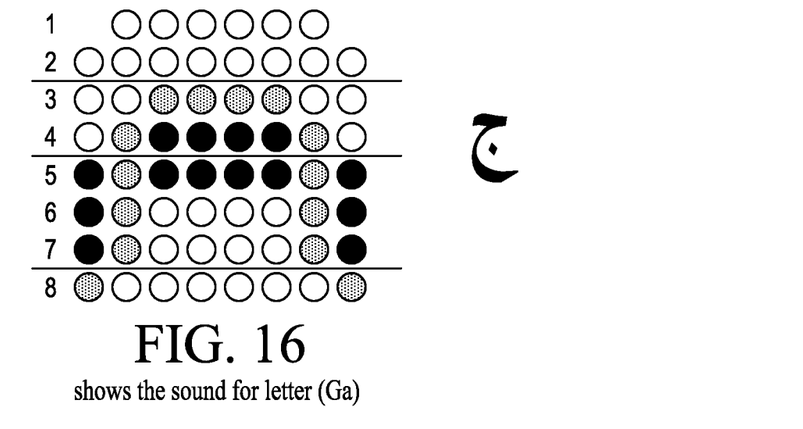
FIG. 16 is a bottom view looking upward at a plurality of pressure points on a palate plate for a thirteenth Arabic letter (Ga)
Figure 17:
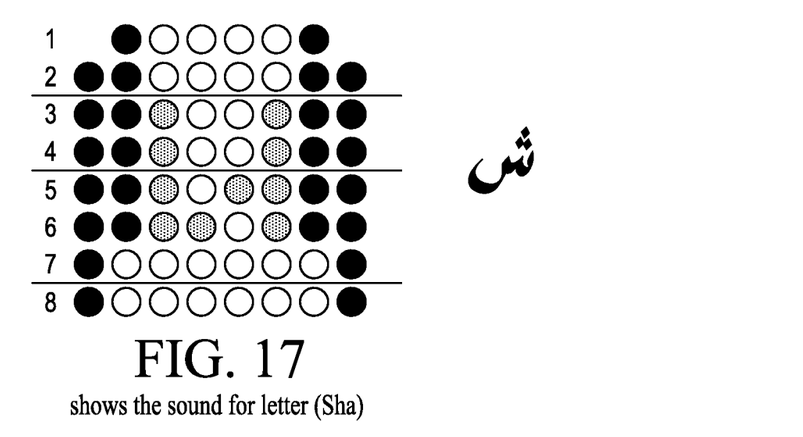
FIG. 17 is a bottom view looking upward at a plurality of pressure points on a palate plate for a fourteenth Arabic letter (Sha)
Figure 18:
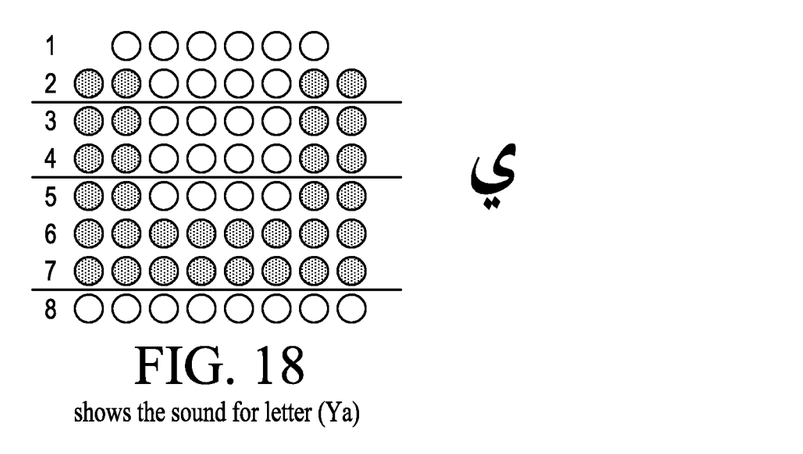
FIG. 18 is a bottom view looking upward at a plurality of pressure points on a palate plate for a fifteenth Arabic letter (Ya)
Figure 19:
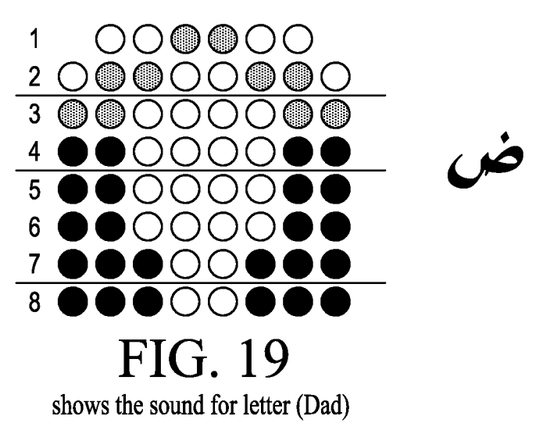
FIG. 19 is a bottom view looking upward at a plurality of pressure points on a palate plate for a sixteenth Arabic letter (Dad)
Figure 20:
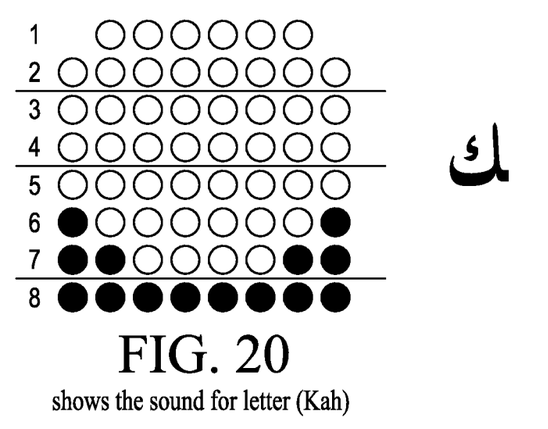
FIG. 20 is a bottom view looking upward at a plurality of pressure points on a palate plate for a seventeenth Arabic letter (Kah).

FIG. 3 shows a metallic wire like support 11 for positioning a palate plate or device in the mouth of an individual. The palate plate is made of a rigid or semi rigid thermoplastic material such as polypropylene or other plastic of the type used for dental retractors or the like.

In a preferred embodiment of the invention, the number of downwardly projecting stubs depends on the articulation of the sound as there are some sounds that require emphasis on the upper lip so that the number of pressure points i.e. short downward projecting stubs is increased. For example, an "L" sound may call for 11 points distributed to the upper lip near the front teeth whereas an "SH" may use 30 projections or small stubs distributed on a palate plate or device.

It should be recognized that the invention does not treat all letters (sounds), but it treats particular letters produced at the gum, from between the teeth and the lips because it is based on the feelings of the tongue to the rough area on a palate plate or device. For example, there are guttural letter sounds such as "a" does not depend on the tongue in its pronunciation therefore the sound articulation determines whether it can be treated or not. FIG. 1 indicates a specific position that sounds and letters produced therefrom can be treated. For example, in the Arabic language the device can treat about 17 letters out of 28 letters noting that the device is not limited for the treatment of Arabic letters only but it treats the letters of all world languages that are produced at the position stated about and indicated in FIG. 1.

The other section of the invention is the software. It is a program that assesses pronunciation and gives a percentage indicating the correctness of the letter pronounced by the user. Also the program compares the pronounced letter with its standard pronunciation. The illustration is presented through animated pictures shows the way of the tongue movement inside the mouth. On the right part of the screen shows a picture indicates the movement of the user's tongue inside the mouth. For example, the program orders the user to pronounce the letter "K". The user wrongly pronounced it "T", the software gives two pictures; one on the right part of the screen shows an animated picture of the "T" letter pronounced by the user. On the other part of the screen, another animated picture will show the standard movement of the tongue for the pronunciation of the letter "K". Also, a percentage will appear with the picture informing the user about the percentage of the correctness of his pronunciation, in addition to other remarks and advices. This software may be used online or to be downloaded on PCs or to use as an application on smart phones. The usefulness of this software is it assists the teacher or the audiology and Speech Pathology Specialist (speech therapist) to follow up the patient after leaving the clinic. Normal persons can download this application to their smart phones and learn correct pronunciation by himself, noting that the efficiency of the software doesn't depend on the device nor does the device depend on the software. Both of them can work independently. It worth mention that the device and the software are appropriate to certain cases where it is recommended to use both of them if the patient wishes to make his treatment easier and faster.

DESCRIPTION OF THE INVENTION

The device consists of two parts. The first part is made of steel. Its function is to fix the device between the teeth. The second part is a material that covers the upper gum. In this case you do not want to make orthodontics. Therefore, upon manufacturing the device, the user can request the steel to be somehow loosened or the substance fixing the device in order not to press on the teeth leaving the teeth in their normal position. The shape of steel is not fixed. Its shape depends on the shape of the teeth as illustrated. Applicant developed a table for the positions of the Arabic language articulation, noting that the positions are subject to change. For example, for the letter "T" and how you place a shape of the dots in the table on the device. In fact, Applicant produced more than eleven pieces and tested them to different patients.

Means of Implementing the Invention

The devices depend on a dental clinic. Any dental clinic specialized in orthodontics, can manually produce a device in a few hours. Additionally, you can provide the dental clinic with positions for the sound articulation. One device is required for each letter and the protrusions are made from the same material as the plate.

Regarding the material used for producing the devices, it is the same material used in removable orthodontics as for example polyethylene, polypropylene, polyterpene and other suitable plastics.

While the invention has been described in connection with the above-identified preferred embodiments, it should be recognized and understood that changes and modifications may be made therein without departing from the scope of the appended claims.

What is claimed is:

1. A method for providing seventeen tongue-pressure-indicating devices, each one of the seventeen devices configured to correct a pronunciation of a different one of seventeen letters in an Arabic alphabet, said method comprising:
    producing seventeen rigid or semi-rigid thermoplastic palate plates of a material selected from the group consisting of: polyethylene, polypropylene, and polyterpene;
        wherein each of said palate plates is configured to be positioned within an individual's mouth to correspond with the individual's palate;
    attaching a metallic wire support to each of said palate plates, wherein the metallic wire support is usable for positioning said palate plate inside of the individual's mouth immediately below and conforming with said individual's palate;
        wherein each of said palate plates indicates a proper position of the individual's tongue against the palate plate for proper pronunciation of a selected one of the seventeen letters in the Arabic alphabet;
    attaching a plurality of non-electrical pressure indicating points on a surface of each of said palate plates, the plurality of non-electrical pressure indicating points consisting of an eight-by-eight pattern of rows and columns wherein each position in the pattern is either empty or occupied by one of:
    a downward projection having a a first height and a stub having a second height, the first height being greater than the second height;
        wherein each of said palate plates includes a combined total of stubs and downward projections, the combined total being at least twelve; and
        wherein a first position in the first row in the first column and a last position in the first row in the eighth column are empty; and
        wherein places where the individual's tongue contacts or presses against a roof of the individual's mouth for proper pronunciation of the selected one of the seventeen letters in the Arabic alphabet include a tip of the individual's tongue rising to an upper palate touching a gum behind two upper front teeth, an alveolar dental area with the tip of the tongue touching the edge of the two upper front teeth, a dental area with the tip of the individual's tongue touching the gum of the two upper front teeth, an alveolar area with the tip of the tongue touching a hard palate, a palatal area where a center of the individual's tongue touches the upper palate, a molar area where upturned sides of the individual's tongue touch a gum of upper back teeth, and in a uvular area where a back of the individual's tongue touches a soft palate.

2. The method of claim 1, wherein at least one of the plurality of devices comprises a configuration in which each position in the first row is empty and each position in the second row is empty.

3. The method of claim 1, wherein at least one of the plurality of devices comprises a configuration in which each position in the first row is empty and the second row consists of four stubs wherein a first position in the second row in the first column is occupied by a first of the four stubs, a seventh position in the second row in the seventh column is occupied by a second of the four stubs, and an eighth position in the second row in the eighth column is occupied by a third of the four stubs.

4. The method of claim 1, wherein at least four of said palate plates include an equal number of stubs and downward projections.

5. The method of claim 1, wherein at least seven of said palate plates include a larger number of downward projections than stubs.

6. The method of claim 1, wherein at least six of said palate plates include a larger number of stubs than downward projections.

7. The method of claim 1, wherein at least three of said palate plates include only stubs.

8. The method of claim 1, wherein at least two of said palate plates include only downward projections.

9. The method of claim 1, wherein for at least two of said palate plates, a majority of the downward projections in the pattern are adjacent to or in either the palatal area or the uvular area.

10. A method for using at least one of seventeen tongue-pressure-indicating devices, each one of the seventeen devices configured to correct a pronunciation of a different one of seventeen letters in an Arabic alphabet, said method comprising:
affixing at least one of seventeen rigid or semi-rigid thermoplastic palate plates in an individual's mouth, the at least one palate plate being of a material selected from the group consisting of: polyethylene, polypropylene, and polyterpene;
wherein a metallic wire support attached to the at least one palate plate is used for positioning said palate plate inside of the individual's mouth immediately below and conforming with said individual's palate;
wherein each of said palate plates indicates a proper position of the individual's tongue against the palate plate for proper pronunciation of a selected one of the seventeen letters in the Arabic alphabet and each of said palate plates includes a plurality of non-electrical pressure indicating points on a surface of said palate plate consisting of an eight-by-eight pattern of rows and columns wherein each position in the pattern is either empty or occupied by one of: a downward projection having a first height and a stub having a second height, the first height being greater than the second height;
wherein at least four of said palate plates include an equal number of stubs and downward projections; and
wherein a first position in the first row in the first column and a last position in the first row in the eighth column are empty;
wherein places where the individual's tongue contacts or presses against a roof of the individual's mouth for proper pronunciation of the selected one of the seventeen letters in the Arabic alphabet include a tip of the individual's tongue rising to an upper palate touching a gum behind two upper front teeth, an alveolar dental area with the tip of the tongue touching the edge of the two upper front teeth, a dental area with the tip of the individual's tongue touching the gum of the two upper front teeth, an alveolar area with the tip of the tongue touching a hard palate, a palatal area where a center of the individual's tongue touches the upper palate, a molar area where upturned sides of the individual's tongue touch a gum of upper back teeth, and in a uvular area where a back of the individual's tongue touches a soft palate; and
producing a sound, by the individual with the at least one palate plate affixed in the individual's mouth, with the individual's tongue contacting at least one downward projection or stub.

11. The method of claim 10, wherein at least seven of said palate plates include a larger number of downward projections than stubs.

12. The method of claim 10, wherein at least six of said palate plates include a larger number of stubs than downward projections.

13. The method of claim 10, wherein at least three of said palate plates include only stubs.

14. The method of claim 10, wherein at least two of said palate plates include only downward projections.

15. The method of claim 10, wherein for at least two of said palate plates, a majority of the downward projections in the pattern are adjacent to or in either the palatal area or the uvular area.

16. A tongue-pressure-indicating system for correcting a pronunciation of a selected letter in a preselected alphabet, said system comprising:
a rigid or semi-rigid thermoplastic palate plate of a material selected from the group consisting of: polyethylene, polypropylene, and polyterpene;
wherein said palate plate is configured to be positioned within an individual's mouth to correspond with the individual's palate,
wherein said palate plate includes a metallic wire support for positioning said palate plate inside of the individual's mouth immediately below and conforming with said individual's palate,
wherein said palate plate indicates a proper position of the individual's tongue against the palate plate for proper pronunciation of a selected letter in the preselected alphabet and said palate plate includes a plurality of non-electrical pressure indicating points on a surface of said palate plate consisting of an eight-by-eight pattern of rows and columns wherein each position in the pattern is either empty or occupied by one of: a downward projection having a first height and a stub having a second height, the first height being greater than the second height,
wherein said palate plate includes a combined total of stubs and downward projections, the combined total being at least twelve,
wherein a first position in the first row in the first column and a last position in the first row in the eighth column are empty, and
wherein places where the individual's tongue contacts or presses against a roof of the individual's mouth for proper pronunciation of the selected letter in the preselected alphabet include a tip of the individual's tongue rising to an upper palate touching a gum behind two upper front teeth, an alveolar dental area with the tip of the tongue touching the edge of the two upper front teeth, a dental area with the tip of the individual's tongue touching the gum of the two upper front teeth, an alveolar area with the tip of the tongue touching a hard palate, a palatal area where a center of the individual's tongue touches the upper palate, a molar area where upturned sides of the individual's tongue touch a gum of upper back teeth, and in a uvular area where a back of the individual's tongue touches a soft palate.

17. The system of claim 16, wherein said palate plate includes an equal number of stubs and downward projections.

18. The system of claim 16, wherein said palate plate includes a larger number of stubs than downward projections.

19. The system of claim 16, wherein said palate plate includes a larger number of downward projections than stubs.

20. The method of claim 16, wherein a majority of the downward projections in the pattern are adjacent to or in either the palatal area or the uvular area.

\* \* \* \* \*